(12) United States Patent
Heidner et al.

(10) Patent No.: US 8,518,103 B2
(45) Date of Patent: Aug. 27, 2013

(54) BIFURCATED DELIVERY SYSTEM AND METHOD

(75) Inventors: Matt Heidner, Maple Grove, MN (US); Karen Turner, Lino Lakes, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1376 days.

(21) Appl. No.: 11/757,657

(22) Filed: Jun. 4, 2007

(65) Prior Publication Data
US 2008/0300666 A1  Dec. 4, 2008

(51) Int. Cl.
*A61F 2/06* (2006.01)

(52) U.S. Cl.
USPC .......................................................... 623/1.35

(58) Field of Classification Search
USPC ........... 623/1.11, 1.12, 1.35; 604/528, 101.1, 604/103.07
See application file for complete search history.

(56) References Cited

U.S. PATENT DOCUMENTS

| | | | |
|---|---|---|---|
| 5,814,016 A * | 9/1998 | Valley et al. ............... | 604/96.01 |
| 6,099,497 A * | 8/2000 | Adams et al. .............. | 604/96.01 |
| 6,146,356 A | 11/2000 | Wang et al. | |
| 6,210,429 B1 | 4/2001 | Vardi et al. | |
| 6,325,826 B1 | 12/2001 | Vardi et al. | |
| 6,692,483 B2 | 2/2004 | Vardi et al. | |
| 6,706,062 B2 | 3/2004 | Vardi et al. | |
| 7,220,275 B2 | 5/2007 | Davidson et al. | |
| 2001/0049548 A1 * | 12/2001 | Vardi et al. ................... | 623/1.11 |
| 2004/0176837 A1 | 9/2004 | Atladottir et al. | |
| 2005/0015108 A1 * | 1/2005 | Williams et al. ............. | 606/194 |

FOREIGN PATENT DOCUMENTS

| | | |
|---|---|---|
| EP | 1683541 | 7/2006 |
| GB | 744327 | 2/1956 |
| WO | 2005046757 | 5/2005 |
| WO | 2007053552 | 5/2007 |

OTHER PUBLICATIONS

U.S. Appl. No. 60/776,149, filed Feb. 22, 2006, Malewicz et al.

* cited by examiner

*Primary Examiner* — Katherine Dowe
(74) *Attorney, Agent, or Firm* — Seager, Tufte & Wickhem LLC

(57) ABSTRACT

A catheter assembly includes an elongate main catheter branch and an elongate side catheter branch. The main catheter branch includes an arc shape and an inflatable balloon extending along a portion of the arc. The side catheter branch extends along the main catheter branch within a plane of the curvature of the arc of the main catheter branch. A stent can be positioned along the inflatable balloon. The stent includes a lateral branch opening through which the side catheter branch extends.

22 Claims, 6 Drawing Sheets

BIFURCATED DELIVERY SYSTEM AND METHOD

TECHNICAL FIELD

This disclosure relates to systems and methods treating bifurcated lumens. Preferred arrangements relate to catheters assemblies used in treatment of vessel bifurcations.

BACKGROUND

Catheters are used with stents and balloon inflatable structures to treat strictures, stenoses, and narrowing in various parts of the body. Various catheter designs have been developed for the dilatation of stenoses and to deliver and deploy stents at treatment sites within the body.

Stents are typically intraluminally placed by a catheter within a vein, artery, or other tubular body organ for treating conditions such as, for example, occlusions, stenoses, aneurysms, dissection, or weakened, diseased, or abnormally dilated vessel or vessel wall, by expanding the vessel or by reinforcing the vessel wall. Stents can improve angioplasty results by preventing elastic recoil and remodeling of the vessel wall and treating dissections in blood vessel walls caused by balloon angioplasty of coronary arteries. Stents can also be used as a drug delivery medium for treatment of damaged portions of a vessel.

While conventional stent technology is relatively well developed, stent technologies related to treatment of the region of a vessel bifurcation are still being developed.

SUMMARY OF THE DISCLOSURE

The present disclosure generally relates to a catheter assembly having an arc portion that includes curved section. The arc portion maintains the curved section when in a rest state. The arc portion assists in radially aligning the catheter assembly relative to a vessel bifurcation. A catheter assembly having an arc portion formed therein can improve self-radially alignment of features of the catheter assembly relative to features of a vessel bifurcation. An example catheter assembly includes a main catheter branch and a side catheter branch. The main catheter branch includes the arc portion. An inflatable balloon can be positioned along at least a portion of the arc portion. The assembly can also include a stent positioned along a portion of the inflatable balloon. The stent can include a lateral branch opening through which the side catheter branch extends.

Another aspect of the present disclosure relates to methods of forming arc portion in a catheter assembly. The arc portion includes a curved section that is maintained in the arc portion when in a rest state. An example method includes inserting a first mandrel into a main catheter branch of the catheter assembly, wherein the first mandrel has an arc shaped portion, and heating the main catheter branch while the first mandrel is inserted. The main catheter branch retains an arc shape corresponding to the shape of the mandrel upon removal of the mandrel. Similar steps can be taken to form an arc portion in a side catheter branch of the catheter assembly.

There is no requirement that an arrangement or method include all features characterized herein to obtain some advantage according to this disclosure.

DETAILED DESCRIPTION

I. Background

This disclosure relates to bifurcation treatment systems and related methods of treating bifurcations in a patient's body. The term bifurcation means a division location from one unit into two or more units. Generally, two types of bifurcations of a body organ include 1) a main tubular member defining a main lumen and a branch tubular member defining a branch lumen that extends or branches off from the main tubular member, wherein the main and branch lumens are in fluid communication with each other, and 2) a primary or main member defining a primary or main lumen (also referred to as a parent lumen) that splits into first and second branch members defining first and second branch lumens. The term lumen means the cavity or bore of a tubular structure such as a tubular organ (e.g., a blood vessel). The term conduit means a channel (e.g., a pipe or tube) through which something such as a fluid is conveyed. The terms lumen and conduit are used interchangeable throughout this document.

An example bifurcation is a vessel bifurcation that includes a continuous main vessel and a branch vessel, wherein the vessels define a main lumen and a branch lumen, respectively that are in fluid communication with each other. A vessel bifurcation can alternatively include a parent vessel that divides into first and second branch vessels, wherein the vessels define a parent lumen and first and second branch lumens, respectively, which lumens are all in fluid communication with each other.

Example applications of the inventive principles disclosed herein include cardiac, coronary, renal, peripheral vascular, gastrointestinal, pulmonary, urinary, and neurovascular systems. The bifurcation delivery systems disclosed herein can be used for locating a branch vessel of the vessel bifurcation. The disclosed systems can also be used for placement of a stent relative to the vessel bifurcation for treatment of the vessel bifurcation. An example vessel bifurcation treatment system in accordance with the present disclosure includes a main guidewire, a main catheter branch, an expandable balloon positioned on the main catheter branch, a side catheter branch, and a stent.

The example vessel bifurcation treatment systems disclosed herein are configured for radial self-alignment within an arc shaped portion of a tubular structure or conduct (e.g., a coronary vessel). An arc portion or arc shape includes a curved section. A curved section can have a variety of shapes such as a radius (also referred to as a radius of curvature). The curved section of an arc portion for purposes of the present disclosure should have a radius of curvature that is less than an infinite value, and preferably less than about 1 m. A curved section having a radius can be structured with a bend or bowed portion such as a portion included in a circular shape, semi-circular shape, oval shape, or semi-oval shape. A curved section can be structured with multiple linear portions that together define a generally arcuate shape. A structure having a curved section has a length along the structure between opposing ends of the structure that is longer than a length of a straight line extending from one end to an opposite end of the structure.

The arc portion of a catheter branch can be defined in the following manner. The arc portion can include a curved section having first and second ends and an exterior surface. The arc portion maintains the curved section when in a rest state as discussed above. The arc portion further includes a lumen defined within the arc portion that extends between the first and second ends along the curved section. The arc portion includes an inwardly curved exterior surface side portion of the curved section and an outwardly curved exterior surface side portion of the curved section. At least one rest side portion of the arc portion is arranged on the exterior surface between the inwardly and outwardly curved exterior surface side portions. The at least one rest side portion is arranged in a plane parallel with a projection plane. The projection plane is oriented parallel to a plane extending from the inwardly curved side portion to the outwardly curved side portion.

In one example vessel bifurcation treatment system, at least the main catheter branch is configured with an arc portion having a curved section. The curved section of an arc portion of a catheter branch can substantially match a bend radius of an arc portion or shape in a main vessel at the treatment site of a vessel bifurcation. Typically, a branch vessel of the vessel bifurcation branches off from the main vessel in a direction within the same plane as the bend or arc shape in the main vessel. The branch vessel also typically branches off from the parent vessel on either the concave side or the convex side of the arc shape in the main vessel (i.e., along an outer side of the arc or along an inner side of the arc shape in the main vessel). The branch vessel typically does not branch off from the parent vessel at a radial location around the circumference on an exterior surface of the parent vessel between the concave and convex sides. However, in some cases the branch vessel does branch off from the parent vessel at radial locations around the circumference of the parent vessel between the concave and convex side. Principles of disclosed vessel bifurcation treatment system disclosed herein can be applied for treatment of such less common branch vessel arrangements as well.

Figures 12, 13:
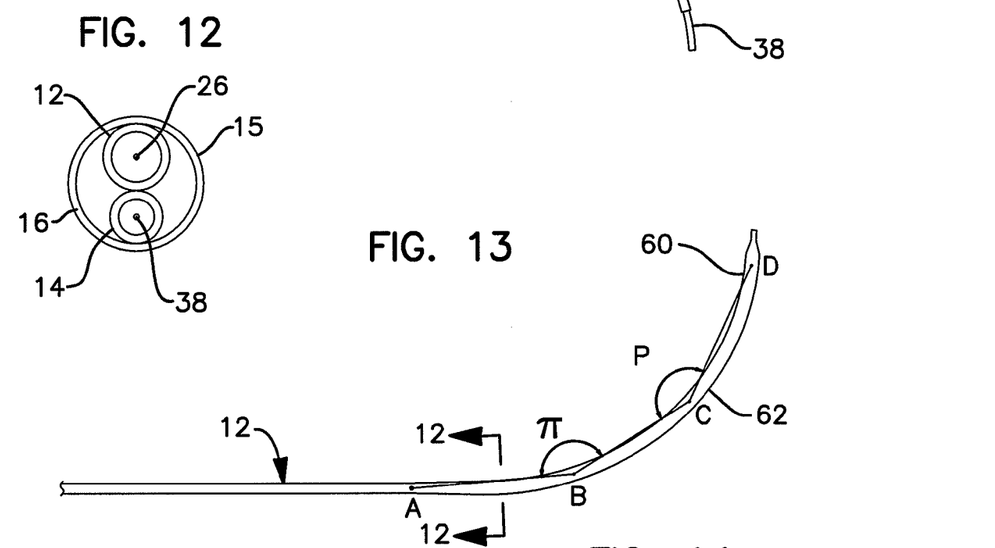
FIG. 12 is an enlarged schematic cross-sectional view of the bifurcation delivery system shown in FIG. 11 taken along cross-sectional indicators 12-12.
FIG. 13 is a schematic representation of the main catheter branch shown in FIG. 1.
Figure 14:
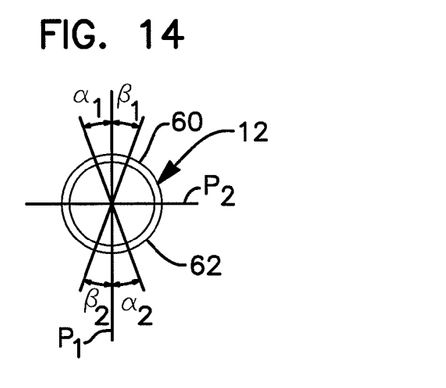
FIG. 14 is an enlarged schematic cross-sectional view of the main catheter branch shown in FIG. 14 taken along indicators 14-14.

Referring now to FIGS. 13 and 14, an example main catheter branch 12 having an arc shaped portion is shown and described. The main catheter branch 12 includes a concave side 60 and a convex side 62. The concave and convex sides 60, 62 are oriented on opposite sides of the main catheter branch 12 from each other within a plane of curvature $P_1$ extending through a central axis of the main catheter branch 12. A radial position around a circumference of the main catheter branch 12 is considered to be on the concave side if the position is within an angle $\alpha_1$ or $\beta_1$ on either side of the plane $P_1$. Likewise, a radial position around the circumference of the main catheter branch 12 is considered to be on the convex side if the position is within an angle $\alpha_2$ or $\beta_2$ on either side of the plane $P_1$. The angles $\alpha_1$, $\beta_1$, $\alpha_2$, $\beta_2$ are typically in the range of about 0° to about 30°. A radial position about the circumference of the main catheter branch 12 outside of the range of radial positions defining the concave and convex sides is considered to be outside of the plane of curvature $P_1$.

The main catheter branch 12 shown in FIG. 12 includes a curved shape that defines an arc or arcuate portion of the main catheter branch 12. An arc portion of an elongate member such as main catheter branch 12 can be defined by a plurality of points along a line that define a non-randomly arcuate portion. In one example, the points along the arc meet a mathematical definition of a circular arc. For equally spaced apart points along the arc, different arc structures can be created by varying the angle defined between straight lines connecting the arc (e.g., see angles $\pi$ and $\rho$ between straight lines connecting points A, B, C, D in FIG. 12).

The side catheter branch of the example vessel bifurcation treatment system is positioned relative to the arc in the main catheter branch to be more easily directed into a branch vessel that is positioned along an arc portion of a main vessel of a vessel bifurcation. For example, the side catheter branch is positioned on a concave side of the main catheter branch arc portion for insertion into a branch vessel that extends from a concave side of the arc portion of the parent vessel. Alternatively, the side catheter branch is positioned on a convex of the main catheter branch arc portion for insertion into a branch vessel that extends from a convex side of the arc portion of the parent vessel.

A wide variety of stents, catheters, and guidewire configurations can be used with the bifurcation delivery system embodiments of the present disclosure. The inventive principles disclosed herein should not be limited to any particular design or configuration.

Some example stents that can be used with the bifurcation delivery systems disclosed herein can be found in, for example, U.S. Pat. Nos. 6,210,429, 6,325,826 and 6,706,062 to Vardi et al., co-pending U.S. patent application Ser. No. 10/644,550, filed on Aug. 21, 2003, and titled STENT WITH A PROTRUDING BRANCH PORTION FOR BIFURCATED VESSELS, and U.S. Published Patent Application No. 2004/0176837 titled SELF-EXPANDING STENT AND CATHETER ASSEMBLY AND METHOD FOR TREAT- ING BIFURCATIONS, the entire contents of which are incorporated herein by reference. In general, the aforementioned stents include a lateral branch opening located between distal and proximal open ends of the stent. The lateral branch opening defines a path between an inner lumen of the stent and an area outside of the stent. The stent lateral branch opening is distinct from the cell openings defined between strut structures from which the stent sidewall is constructed. In some stents, the lateral branch opening can be surrounded by expandable structure. The expandable structure can be configured to extend radially into the branch lumen of the bifurcation upon expansion of, for example, an inflatable portion of the bifurcation treatment system. Typically, the stent is expanded after being positioned in the main lumen with the lateral branch opening aligned with an opening into the branch lumen. Alignment of the lateral branch opening with the opening into the branch lumen includes both radial and axial alignment. The stent, including the expandable structure surrounding the lateral branch opening, can be expanded with a single expansion or multiple expansions using one or more inflatable members.

The arc portion of the main and side catheter branches described and illustrated with reference to the Figures reflects a permanent or fixed shape of the catheter branches when in a rest state. A rest state is a state in which no outside forces are applied to the catheter branches to distort the shape of the catheter branches. When the catheter branches are advanced over guidewires, the stiffness of the guidewires can be greater than the stiffness of the catheter branches thereby imposing a force that tends to distort the shape of the catheter branches from their rest state shape. As a result, the appearance of the catheter branches with the guidewire inserted may appear to not include the arc shape usually visible when the guidewires are removed. However, a catheter branch having a permanent arc portion has a propensity to rotate into a rest state, especially when the catheter branches and guidewires are positioned within an arc shaped vessel in a radial orientation that does not match the rest state of the catheter branch arc portion. Thus, catheter branches with arc shapes formed therein can still have the advantageous self-radially aligning characteristics described herein even when an external force (e.g., straight guidewire) is applied to move the catheter branch arc portion out of its rest state position.

II. The Example Illustrated in FIGS. 1-2

Figure 1:
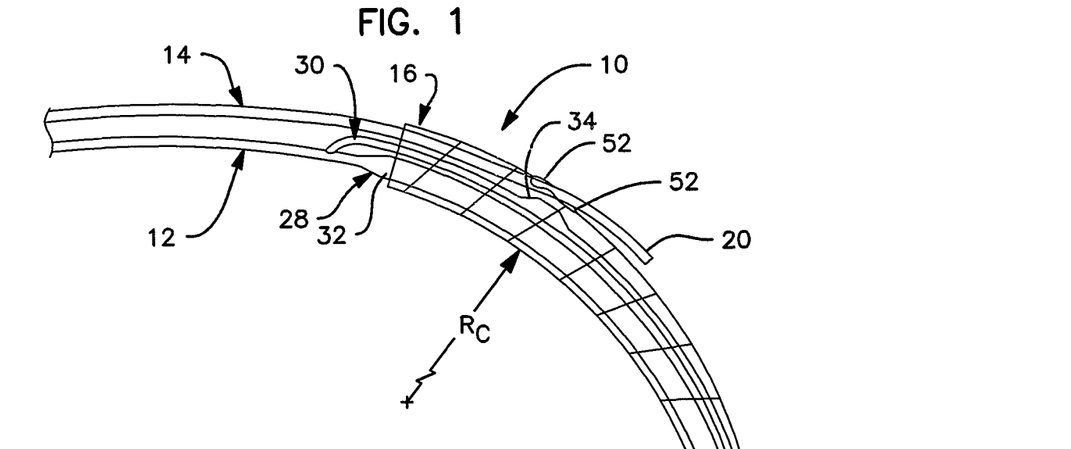
FIG. 1 is a schematic representation of an exemplary bifurcation delivery system constructed with a main catheter branch having an arc portion and having a side catheter branch positioned at a convex side of the arc portion.
Figures 2, 2A:
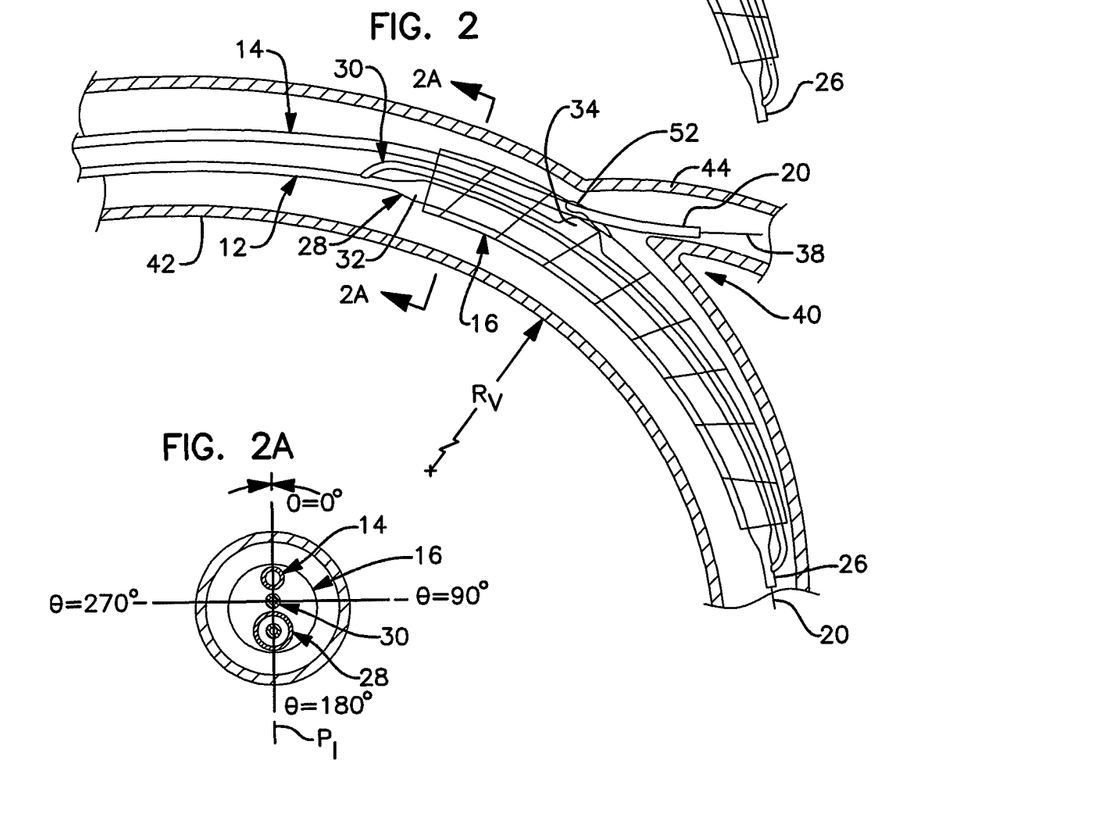
FIG. 2 is a schematic representation of the bifurcation delivery system shown in FIG. 1 positioned adjacent to a vessel bifurcation.
FIG. 2A is a schematic cross-sectional view of the bifurcation delivery System shown in FIG. 2 taken along cross-sectional indicators 2A-2A.

A schematic illustration of an example bifurcation delivery system 10 is shown in FIGS. 1-2. Bifurcation delivery system 10 includes a main catheter branch 12, a side catheter branch 14, and a stent 16. The main catheter branch 12 defines a main branch lumen and includes an arc shape having a catheter radius $R_C$. The main catheter branch 12 has a distal tip 26. The stent 16 is positioned along the main catheter branch 12 proximal of the distal tip. The side catheter branch 14 defines a side branch lumen and includes a distal end 20. The side catheter branch 14 is arranged along a convex side of the arc shape of main catheter branch 12. The side catheter branch 14 is configured and arranged to extend through a proximal interior portion of the stent in a side-by-side relationship with the main catheter branch 12. The side catheter branch 14 is shown having a linear shape without an arc portion formed therein. Some example side catheter branch having arc portions are described below with reference to FIGS. 7-10.

In general, an elongate structure having an arc portion tends to move towards a rest state wherein a plane of the arc portion (e.g., plate $P_1$ shown in FIG. 12) is orientated in parallel with a top surface upon which the elongate structure rests. For example, an elongate member having an arc portion that rests upon a horizontally arranged planar surface will typically rotate into a position wherein a plane of the arc portion (e.g., $P_1$) aligns parallel with the plane of the horizontal surface. Further, an elongate structure having an arc shape portion when positioned within an elongate lumen or conduit also having an arc shape portion tends to rotate until the plane of curvature of the elongate structure is co-planar with the plane of curvature of the elongate lumen or conduit. Thus, when a catheter branch having an arc shape portion is positioned within a vessel branch having an arc shape portion, the catheter shaft tends to rotate toward a position in which a plane of curvature of the catheter arc is aligned co-planar with a plane of curvature of the arc portion in the vessel branch.

Providing an arc shape portion in the main catheter branch 12 having a radius of curvature that matches a radius of curvature of an arc shape portion of the main vessel of a vessel bifurcation can help the bifurcation delivery system 10 self-align radially relative to a branch vessel of the vessel bifurcation. The self-alignment of the main catheter branch 12 relative to the vessel bifurcation can occur in part because the arc shape portion in the main catheter branch helps the main catheter branch move itself radially until the arc portion of the main catheter branch aligns in the same plane and arcing in the same curvature direction as the plane and curvature direction of the arc portion of the main vessel.

This propensity of the main catheter branch 12 to self-align radially with the arc portion of a main vessel can be used in combination with positioning of the side catheter branch 14 relative to the arc portion of the main catheter branch 12 to align the side catheter branch 14 with the branch vessel of the vessel bifurcation. For example, if a vessel bifurcation includes a main vessel with an arc portion and a branch vessel extending from convex side of the arc portion, the side catheter branch can be positioned along a convex side of the main catheter branch arc (see FIGS. 1-2). In another example, the side catheter branch can be positioned along a concave side of the main catheter branch arc to match with a position of the branch vessel of the vessel bifurcation extending from a concave side of the main vessel arc portion (see FIGS. 3-4). Thus, when the main catheter branch has rotated itself into a rest state within the main vessel (i.e., the plane and direction of curvature of the main catheter branch arc portion is aligned with a plane and direction of curvature of the main vessel arc portion), the side catheter branch is oriented radially relative to an ostium of the branch vessel.

The self-radially aligning aspects of a bifurcation delivery system having an arc portion can be particularly useful when the bifurcation delivery system is used with multiple guidewires. The use of multiple guidewires within a single vessel can result in crossed-over and relative twist between the guidewires. Relative twist between guidewires can result in misalignment of features of the bifurcation delivery system relative to the main and branch vessels of a vessel bifurcation. Relative twist between guidewires can also inhibit advancement of the bifurcation delivery system over the guidewires to the vessel bifurcation. A bifurcation delivery system having an arc portion as disclosed herein can be particularly useful for overcoming cross-over and relative twist disadvantages common with two-guidewire systems. The use of an arc portion in a bifurcation delivery system when the guidewires have at least 180° of relative twist can be effective at providing proper alignment of features of the bifurcation delivery system with a branch vessel of the vessel bifurcation. When the guidewires have at least about 360° of relative twist, or even as much as about 720° or more relative twist, the arc portion in a bifurcation delivery system is especially effective at self-radial alignment.

Referring again to FIG. 1, one example bifurcation delivery system 10 includes a main catheter branch 12 having first and second branches 28, 30. A main inflatable portion 32 is positioned on the first branch 28, and an auxiliary inflatable portion 34 is positioned on the second branch 30. The second branch 30 branches off of the first branch portion 28 proximal of the main inflatable portion 32. The second branch 30 is shown extending substantially parallel with the main inflatable portion 32 along much of the length of second branch 30. A distal end of the second branch 30 is attached to the first branch 28 distal of the main inflatable portion 32. The second branch 30 is arranged along a convex side of the arc shaped portion of the main catheter branch 12.

The main inflatable portion 32 is generally cylindrical and extends coaxially with a guidewire lumen (not shown) that extends within main catheter branch 12. The second balloon branch 30 can have a size and shape adapted to at least partially expand through a side opening 52 in a sidewall of the stent 16. The auxiliary inflatable portion 34 of the second branch 30 can have a generally hemispherical configuration when inflated. The auxiliary inflatable portion 34 typically extends radially through the side opening 52 in the stent 16 when the inflatable portion 34 is inflated. The auxiliary inflatable portion 34 is arranged facing radially outward from the main catheter branch 12 along the convex side of the arc shape in main catheter branch 12.

In an alternative example, the main catheter branch 12 can have a single branch that includes the first and second inflatable portions 32, 34. In this example, the second inflatable portion is arranged radially on an exterior of the first inflatable portion 32 that is oriented facing an opening into the branch vessel of the vessel bifurcation when the main catheter branch 12 is position in the main vessel and the arc portion of the main catheter branch 12 is aligned in the same plane and facing the same curvature direction as the plane and curvature direction of the main vessel. The second inflatable portion 34 can be integrally formed with the first inflatable portion 32. A balloon having the second inflatable portion 34 integrated into an exterior surface of the first inflatable portion 34 is sometimes referred to as a "blister" or "bulge" type balloon.

The inflatable portions 32, 34 can be balloon expandable members. The inflatable portions 32, 34 and all other balloons disclosed herein can be made of any suitable balloon material including compliant and non-compliant materials and combinations thereof. Some example materials for the balloons and catheters disclosed herein include thermoplastic polymers, polyethylene (high density, low density, intermediate density, linear low density), various co-polymers and blends of polyethylene, ionomers, polyesters, polycarbonates, polyamides, poly-vinyl chloride, acrylonitrile-butadiene-styrene copolymers, polyether-polyester copolymers, and polyetherpolyamide copolymers. One suitable material is Surlyn®, a copolymer polyolefin material (DuPont de Nemours, Wilmington, Del.). Still further suitable materials include thermoplastic polymers and thermoset polymeric materials, poly(ethylene terephthalate) (commonly referred to as PET), thermoplastic polyamide, polyphenylene sulfides, polypropylene. Some other example materials include polyurethanes and block copolymers, such as polyamide-polyether block copolymers or amide-tetramethylene glycol copolymers. Additional examples include the PEBAX® (a polyamide/polyether/polyester block copolymer) family of polymers, e.g., PEBAX® 70D, 72D, 2533, 5533, 6333, 7033, or 7233 (available from Elf AtoChem, Philadelphia, Pa.). Other examples include nylons, such as aliphatic nylons, for example, Vestamid L2101 1F, Nylon 11 (Elf Atochem), Nylon 6 (Allied Signal), Nylon 6/10 (BASF), Nylon 6/12 (Ashley Polymers), or Nylon 12. Additional examples of nylons include aromatic nylons, such as Grivory (EMS) and Nylon MXD-6. Other nylons and/or combinations of nylons can also be used. Still further examples include polybutylene terephthalate (PBT), such as CELANEX® (available from Ticona, Summit, N.J.), polyester/ether block copolymers such as ARNITEL® (available from DSM, Erionspilla, Ind.), e.g., ARNITEL® EM740, aromatic amides such as Trogamid (PA6-3-T, Degussa), and thermoplastic elastomers such as HYTREL® (Dupont de Nemours, Wilmington, Del.). In some embodiments, the PEBAX®, HYTREL®, and ARNITEL® materials have a Shore D hardness of about 45D to about 82D. The balloon materials can be used pure or as blends. For example, a blend may include a PBT and one or more PBT thermoplastic elastomers, such as RITEFLEX® (available from Ticona), ARNITEL®, or HYTREL®, or polyethylene terephthalate (PET) and a thermoplastic elastomer, such as a PBT thermoplastic elastomer. Additional examples of balloon material can be found in U.S. Pat. No. 6,146,356, which is incorporated herein by reference.

The first and second branches 28, 30 are coupled in fluid communication with a common inflation lumen defined by the main catheter branch 12. The inflation lumen extends distally from a proximal end (not shown) of the bifurcation delivery system that remains outside of the patient to the first and second branches 28, 30. The common inflation lumen feeds both of the first and second branches 28, 30. The common inflation lumen is used to supply pressurized inflation fluid to the main and auxiliary inflatable portions 32, 34 when expanding the portions 32, 34. The common inflation lumen is also used to drain inflation fluid from the portions 32, 34 during deflation. The first and second branches 28, 30 are initially deflated when directing the bifurcation delivery system 10 to the treatment site at the vessel bifurcation. The first and second branches 28, 30 can be inflated substantially simultaneously. In other embodiments, a delay can occur between inflation of each of the inflatable portions 32, 34.

The main catheter branch 12 typically defines or includes a separate conduit or structure that defines a guidewire lumen (not shown) sized to receive a main guidewire 36. Typically, a guidewire lumen in the main catheter branch 12 is distinct and separate from the inflation lumen used to supply inflation fluid to the main and auxiliary inflatable portions 32, 34. An example guidewire 36 is shown in FIG. 2 extending from the distal tip 16 of the main catheter branch 12. The guidewire 36 is usually positioned within a main vessel 42 distally of the vessel bifurcation, a proximal end of the guidewire 36 is inserted into a distal end opening of the guidewire lumen at the distal end 26, and then the main catheter branch 12 is advanced over the guidewire 36 to the vessel bifurcation.

The side catheter branch 14 defines an internal lumen (not shown) sized to travel over a branch guidewire such as guidewire 38 shown in FIG. 2. Guidewire 38 is shown extending from the distal tip 20 of the side catheter branch 14. Although the example side catheter branch 14 shown in FIGS. 1-3 does not include an inflatable portion, alternative side catheter branches can include an inflatable portion. A side catheter branch having an inflatable portion is described in co-pending U.S. patent application Ser. No. 10/644,550, entitled STENT WITH A PROTRUDING BRANCH PORTION FOR BIFURCATING VESSELS, which application is incorporated herein by reference. In operation, the side catheter branch 14 extends through the side opening 52 of the stent 16. A distal end of the side catheter branch 14 is positioned adjacent to the stent 16 during delivery of the system 10 to the vessel bifurcation. Typically, the guidewire 38 is first positioned within the branch vessel 44 of a vessel bifurcation, a proximal end of the guidewire 38 is inserted into the distal tip 20, and then the side catheter branch 14 is advanced over the guidewire 38 to the vessel bifurcation. The distal end of the side catheter branch 14 that extends out of the stent side opening 52 is directed along the guidewire 38 into the branch vessel 44 as the side catheter branch 14 is advanced over the guidewire 38.

The side opening 52 is arranged in the example shown in FIGS. 1 and 2 along the convex side of the arc shape of the main catheter branch 12. The side opening 52 is typically arranged both axially and radially in alignment with the auxiliary inflatable portion 34 of the second branch 30 before introducing the system 10 into the patient. The stent 16 is typically releasably secured to the inflatable portions 32, 34 using, for example, a crimp connection. The stent is usually released from the inflatable portions 32, 34 during inflation of the portions 32, 34.

Figure 11:
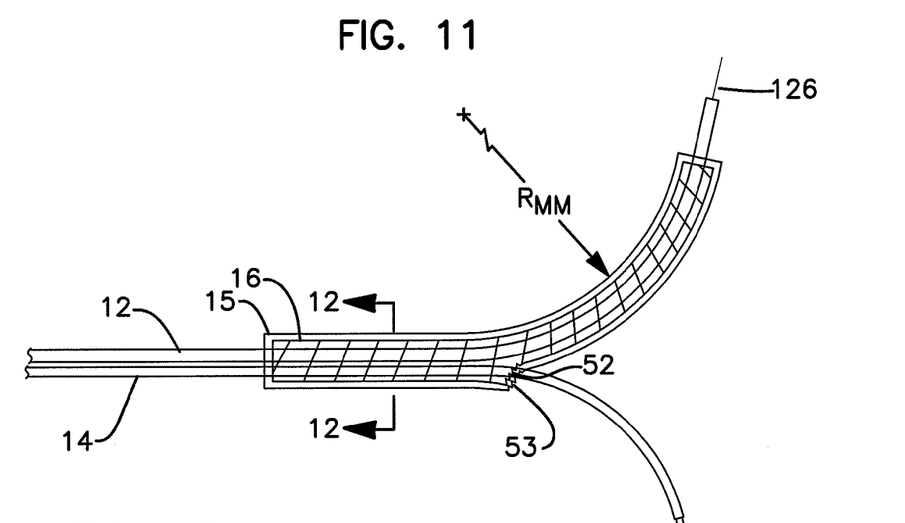
FIG. 11 is a schematic representation of another example bifurcation delivery system having a self-expanding stent.

Alternative bifurcation delivery systems are configured for use with stents having self-expanding features. Self-expanding stents and self-expanding features of a stent typically do not require the use of an inflatable member such as a balloon to expand the sent or stent feature. Typically, self-expanding stents, such as those stents described in U.S. Published Patent Application No. 2004/0176837, are held in a constricted state using a sheath that fits over the stent. In the constricted state, the stent is able to navigate through a body lumen to the treatment site. Once the stent and sheath are positioned at the treatment side, the sheath is retracted proximally to release the stent for expansion of the stent into a radially expanded state. FIGS. 11 and 12 illustrate an example catheter assembly having a self-expanding stent 16 positioned along a main catheter branch 12 and side catheter branch 14, and surrounded by a sheath 15. The sheath 15 and stent 16 can include lateral branch openings 52, 53 through which the side catheter branch 14 extends. The sheath 15 can additionally include a longitudinal opening (e.g., slot or slit shaped opening) that extends from the lateral branch opening 53 to a distal end of the sheath 15 to permit proximal retraction of the sheath 15 relative to the stent 16 and side catheter branch 14. The longitudinal opening (not shown) in the sheath 15 can be retained closed using, for example, a fastener arrangement that is released before attempting to proximally retract the sheath 15.

FIG. 2 illustrates bifurcation delivery system 10 in relation to a vessel bifurcation 40. The vessel bifurcation 40 is defined as the general area in which a branch vessel 44 branches off from a main vessel 42. An opening or ostium is defined in a sidewall of the main vessel 42 at the location where the branch vessel 44 is connected in flow communication with the main vessel 42.

When using the bifurcation delivery system 10 to treat the vessel bifurcation 40, the guidewire 36 is typically first navigated to the treatment site with a distal end of guidewire 36 positioned within the main vessel 42 distal of the ostium of the branch vessel 44. The guidewire 38 is also navigated to the treatment site and then positioned within the branch vessel 44. The physician determines the bend radius of the main vessel arc to help in the selection of a main catheter branch having an arc portion with a suitable radius of curvature. The physician also determines at what circumferential position the branch vessel branches off from the main vessel (e.g., on the convex side, on the concave side, or at some circumferential position between the concave and convex sides as defined with reference to FIGS. 12 and 13). Some types of vessels, such as coronary vessels, typically have branch vessel that branch off from the main vessel within a plane of the arc portion of the main vessel (e.g., plane $P_1$ in FIG. 13). Thus, the branch vessel usually branches off on the concave or convex side of the main vessel arc portion. In other types of vessels, the branch vessel branches off from the main vessel outside of a plane of the arc portion of the main vessel, such as in a plane that is about 0° to about 90° out of the plane of the arc portion of the main vessel. In alternative bifurcation treatment systems (not shown), the side catheter branch is also aligned out of the plane of the arc portion of the main catheter branch to substantially match the anatomy of vessel bifurcation.

Once the radial position of the branch vessel has been determined relative to the arc portion of the main vessel, the physician can select a bifurcation treatment system that substantially matches the anatomy of vessel bifurcation. FIG. 2 illustrates one example of matching the arc portion of the system 10 to an arc portion of the vessel bifurcation 40. It is recognized that a single bend radius size for the bifurcation treatment system 10 can be used for many different vessel bifurcation anatomies.

After selection of the appropriate bifurcation treatment system 10, the proximal end of the guidewire 36 is inserted into the distal end of the main catheter branch 12 and the proximal end of the guidewire 38 is inserted into the distal end of the side catheter branch 14. The bifurcation delivery system 10 is then advanced over the guidewires 36, 38 into a position adjacent to the vessel bifurcation 40. In some treatment methods, the guidewire 36 or the guidewire 38 is navigated through the system 10 to the treatment site at the vessel bifurcation 40 after the system 10 has been advanced over the other of the guidewire 36 or guidewire 38 to the vessel bifurcation 40. Once the guidewire 36 has been positioned with a distal end thereof extending past the bifurcation 40, the guidewire 36 typically remains in the maim vessel 42 until treatment of the vessel bifurcation 40 is complete.

A main catheter branch 12 having an arc portion can assist in radially aligning the stent lateral branch opening 52 in a direction facing the ostium of the branch vessel 44. As described above, the arc of the main catheter branch 12 will typically move to a rest state orientation that is parallel with a plane of the arc portion in the main catheter branch 12. Furthermore, the main catheter branch 12 will not reach a complete rest state until the curvature of the arc portion of the main catheter branch 12 is also aligned facing the same direction as the curvature of the arc portion in the main vessel 12. This complete rest state (i.e., parallel alignment of the planes of the arc portions of the main vessel and main catheter branch, and the curvature of the arc portions of the main vessel and main catheter branch facing the same direction) can be considered a 0° radial position of the plane of the main catheter branch arc portion relative to the and main vessel arc portion. FIG. 2A illustrates this complete rest state with angle $\theta=0°$. Thus, if the main catheter branch 12 is at a radial position greater than $\theta=0°$ and less than $\theta=90°$, or greater than $\theta=270°$ and less than $\theta=360°$, the main catheter branch 12 will tend to move back to the $\theta=0°$ orientation (see FIG. 2A). If the main catheter branch 12 is at a radial position greater than $\theta=90°$ and less than $\theta=180°$, or greater than $\theta=180°$ and less than $\theta=270°$, the main catheter branch 12 will tend to move to the 180° orientation (not shown).

When the main catheter branch 12 is in the $\theta=180°$ position, the arc of the main catheter branch 12 is within the same plane as the arc of the main vessel 42, but curved in a direction opposite to the arc in main vessel 42. In the $\theta=180°$ orientation, the main catheter branch 12 is not in the complete rest state. As a result, the main catheter branch 12 typically can be more easily adjusted radially by the physician to the $\theta=0°$ orientation because the curvature of the arc portion of the main catheter branch 12 is facing in a direction opposite the direction of curvature of the arc portion of the main vessel 42 and actively seeks the complete rest state with the application of relatively little outside rotational force by the physician.

In the example of FIGS. 1-2, the main vessel 42 has a vessel radius of curvature $R_V$ and the main catheter branch 12 has a radius of curvature $R_C$. Preferably, the value $R_C$ is selected to be substantially the same as the value of $R_V$. Typically, the value of $R_C$ is selected to be within about 30% to about 200% of the value of $R_V$, and more preferably about 50% to about 100% of the value of $R_V$, as the curvature of the catheter can be larger or smaller than the curvature of the vessel.

After the bifurcation delivery system 10 is oriented with the side catheter 14 and lateral branch opening 52 facing in a direction toward the ostium of branch vessel 44, the distal end 20 of the side catheter branch 14 is positioned in the branch vessel 44. Typically, when the distal end of the side catheter branch 14 is positioned within the branch vessel 44, the opening 52 of stent 16 is at least partially aligned both axially and radially relative to the ostium of branch vessel 44. The inflatable portion 32 can then be inflated to expand the main body of the stent 16 for treatment of the vessel bifurcation 40. The inflatable portion 34 can also be inflated to treat portions of the vessel bifurcation 40. For example, the inflatable portion 34 can at least partially expand any expandable structure surrounding or otherwise defining the lateral branch opening 52 in a direction towards the branch vessel 44. After inflating the first and second inflatable portions 32, 34 to expand the stent, the inflatable portions 32, 34 are deflated and the main and side catheter branches 12, 14 retracted proximally from the patient. The vessel bifurcation 40 can be treated further using additional inflatable members and stent structure. For example, a branch vessel stent mounted to a branch inflatable member can be advanced over the branch guidewire 38 and through the lateral branch opening 52, wherein the branch inflatable member is inflated to expand the branch stent within the branch vessel 44. Such a branch stent when expanded can also further expand the expandable structure surrounding the lateral branch opening 52 into engagement with the branch vessel 44.

The bifurcation delivery system 10 can include marker material that is visible under X-ray or in fluoroscopy procedures. Any features of the system 10 that include marker material can be more easily identified and distinguished under X-ray or in fluoroscopy procedures. Some example marker materials include gold, platinum and tungsten. In one embodiment, the marker material can be included in a band structure that is secured to at least one of the main and side catheter branches 12, 14. In other embodiments, the marker material is part of the material composition of portions of the main and side catheter branches 12, 14. Viewability of features of the bifurcation delivery system 10 under X-ray or fluoroscopy can assist the physician operating the system 10 to more easily adjust a position of the system 10 relative to the vessel bifurcation 40. Example markers and marker materials suitable for use with system 10 are described in U.S. Pat. No. 6,692,483 to Vardi, et al., and co-pending U.S. provisional patent application Ser. No. 60/776,149, filed on Feb. 22, 2006, and titled MARKER ARRANGEMENT FOR BIFURCATION CATHETER, which patent matters are incorporated herein by reference.

III. The Example Illustrated in FIGS. 3-4

Figures 3, 4:
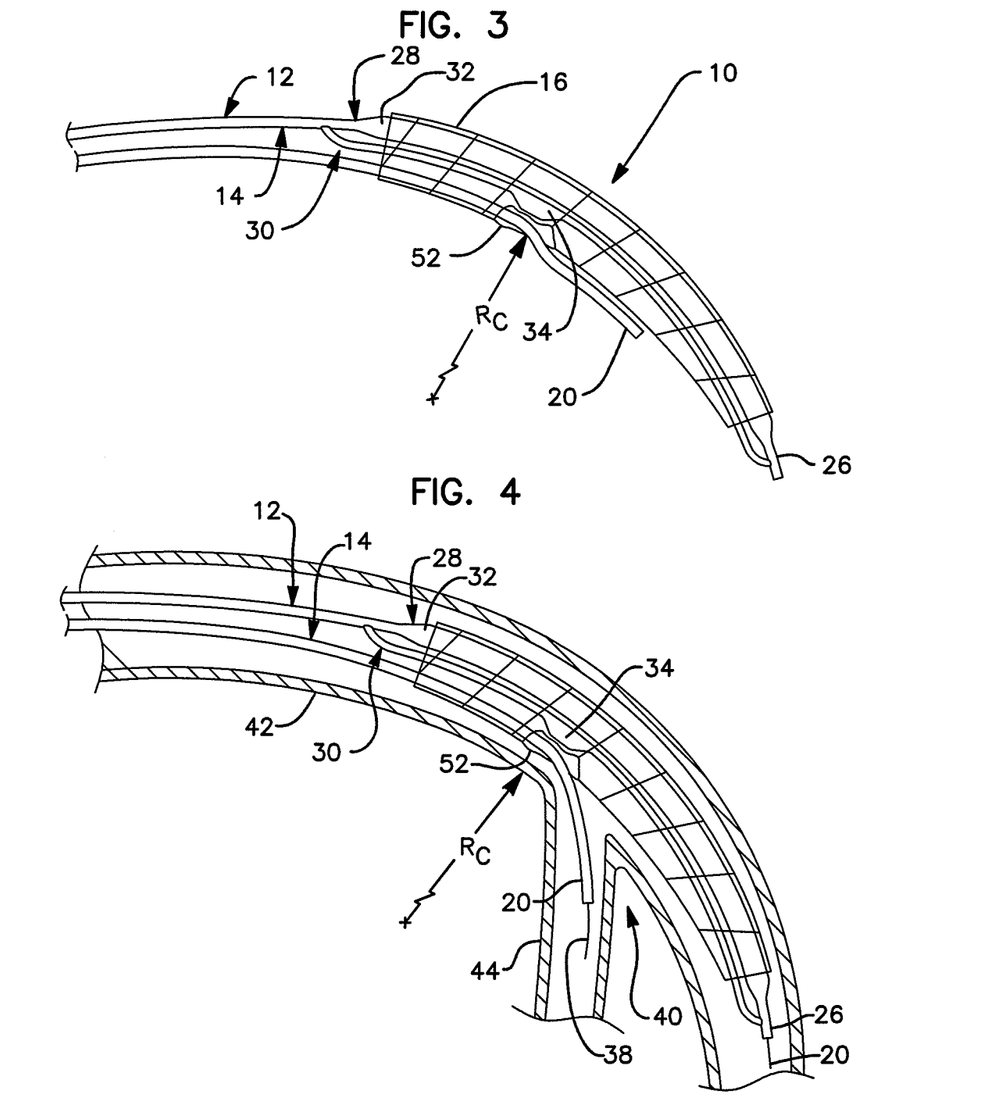
FIG. 3 is a schematic representation of another example bifurcation delivery system constructed with a main catheter branch having an arc portion and having a side catheter branch positioned at a concave side of the arc portion.
FIG. 4 is a schematic representation of the bifurcation delivery system shown in FIG. 1 positioned adjacent to a vessel bifurcation.

FIGS. 3-4 illustrate another example bifurcation delivery system 10. The system 10 of FIGS. 3-4 includes a side catheter branch 14 that is arranged along a concave side of the arc portion of main catheter branch 12. The second branch 30 and auxiliary inflatable portion 34 are also arranged along the concave side of the arc shape in main catheter branch 12. Further, the lateral branch opening 52 of stent 16 is arranged facing radially outward along the concave side of the arc shape in main catheter branch 12. The opening 52 is sized for the side catheter branch 14 to pass through the opening 52 and into the branch vessel 44.

The embodiment of FIGS. 3-4 illustrates use of the bifurcation delivery system 10 with a vessel bifurcation in which the branch vessel 44 is arranged on a concave side of the arc portion of the main vessel 42. The main vessel 42 has a vessel radius of curvature $R_V$ and the main catheter branch 12 has a radius of curvature $R_C$. Preferably, the radius $R_C$ is substantially the same as the $R_V$. Providing the main catheter branch 12 with the arc shape preferably provides at least some self-radial alignment of the side catheter branch 14, stent lateral branch opening 52, and auxiliary inflatable portion 34 with the ostium of branch vessel 44, as described above with reference to FIGS. 1-2.

As described above with reference to FIGS. 1-2, the arc shape of main catheter branch 12 typically leads to self-induced radial movement of the main catheter branch 12 towards a rest state on a support surface in which a plane of the bend in main catheter branch 12 is parallel with the plane of the contact surface. When positioned in a vessel having an arc shape portion, the main catheter branch 12 attains a complete rest state when the curvature of the arc portion of the main catheter branch is facing in the same direction as the curvature of the arc portion of the vessel and the plane of the arc portion of the main catheter branch is aligned parallel with the plane of the arc portion of the vessel.

When the bifurcation delivery system 10 is advanced over guidewires 36, 38 to a treatment site at the vessel bifurcation 40 (see FIG. 4), the main catheter branch 12 will tend to move towards a complete rest state wherein the side catheter branch 14 and stent lateral branch opening 52 are arranged in the plane of the arc portion of the main catheter branch 12 and in the plane of the arc portion of the main vessel 42. The side catheter branch 14 and opening 52 are also shown in FIG. 4 facing or extending in the same direction as the curvature of the arc portion of the main vessel 42 is facing. The arc shape of main catheter branch 12 can assist in obtaining and maintaining radial alignment of the side catheter branch 14 and stent lateral branch opening 52 with the ostium of branch vessel 44.

After the bifurcation delivery system 10 is oriented with the side catheter 14 and opening 52 facing in a direction toward the ostium of branch vessel 44, the system 10 is advanced distally until the distal end 20 of the side catheter branch 14 is positioned in the branch vessel 44. The system 10 can then be advanced distally until resistance in distal movement is felt by the physician resulting from engagement of the side catheter branch 14 with a carina (i.e., distal junction point between the main and branch vessels 42, 44) of the vessel bifurcation 40. With the bifurcation delivery system 10 in this position, the opening 52 of stent 16 is at least partially aligned both axially and radially relative to the ostium of branch vessel 44. The inflatable portion 32 can then be inflated to expand the main body of the stent 16 for treatment of the vessel bifurcation 40. The inflatable portion 34 can also be inflated to treat portions of the vessel bifurcation 40. For example, the inflatable portion 34 can expand any expandable structure surrounding the opening 52 in a radially outward direction into the branch vessel 44. The inflatable portion 34 can also be used to enlarge a size of the opening 52.

IV. The Example Illustrated in FIGS. 5-6

Figure 5:
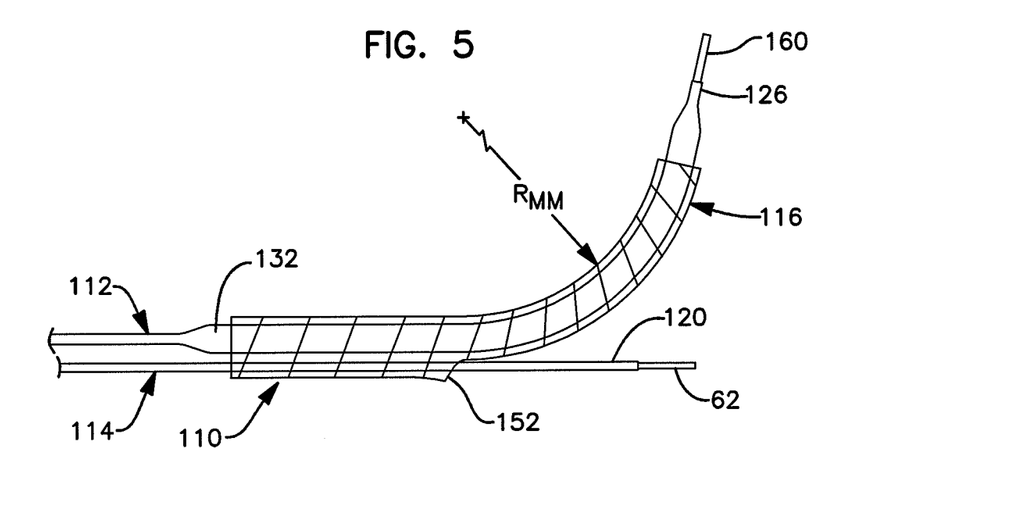
FIG. 5 is a schematic representation of another example bifurcation delivery system having a first portion positioned on a first mandrel having an arc shape portion and a second portion positioned on a second mandrel having a linear shape.
Figure 6:
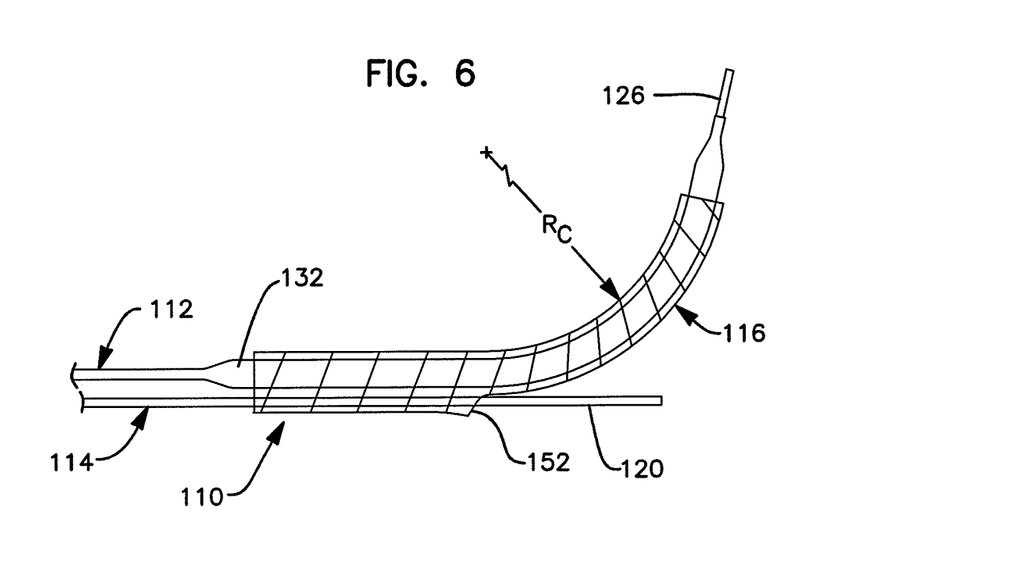
FIG. 6 is a schematic representation of the bifurcation delivery system shown in FIG. 5 with the mandrels removed.

FIGS. 5-6 illustrate aspects of forming an arc shape portion in an example bifurcation delivery system 110. The bifurcation delivery system 110 includes a main catheter branch 112, a side catheter branch 114, and a stent 116. The main catheter branch 112 includes a distal end 126. An inflatable portion 132 is positioned on the main catheter proximal of the distal end 126. The side catheter branch 114 includes a distal end 120. The side catheter branch 114 extends through a lateral branch opening 152 in the stent 116. The methods described below explain how an arc shape portion can be formed in the main catheter branch 112 when the main catheter branch 112 is in a rest state. The side catheter branch 114 includes a generally linear shape when in a rest state.

To set the arc shape portion in the main and maintain the linear shape in the side catheter branch, the bifurcation delivery system 110 is heat set using shaped mandrels that are inserted into the main and side catheter branches 112, 114. A first mandrel 160 having a main mandrel radius of curvature $R_{MM}$ is inserted into the main catheter branch 112. A second mandrel 162 having a linear shape is inserted into the side catheter branch 114. The bifurcation delivery system 110 with the mandrels inserted is then heated for a predetermined time and cooled to set the mandrel shapes in the catheter branches 112, 114.

Known heat setting techniques can be used to perform heat setting of the arc shape portion in the bifurcation delivery system 110. The duration and temperature for heat setting the bifurcation delivery system is dependant on, for example, the type of material used in the catheter branches, the thickness of the material, and the material of the mandrels. The material used in the stent 116 and inflatable portion 132 can also influence the duration and temperature required for heat setting the bifurcation delivery system. Some example materials for use in the catheter branches of the bifurcation delivery system include Nylon, thermoplastic elastomer (TPE), polychlorotrifluoroethylene (PTFE), low density polyethylene (LDPE), and high density polyethylene (HDPE). Some example materials used for the inflatable portion 132 are described above with reference to inflatable portions 32, 34. The time duration for heat setting the bifurcation delivery system can be in the range of a few minutes up to 4-24 hours or longer. The temperature for heat setting is typically in the range of about 30° to about 150° C., while higher temperatures may be required in some cases.

Typically, the temperature and duration required to heat set a shape in the bifurcation delivery system is chosen based on the materials in the system having the greatest resistance to heat setting. For example, the main catheter branch 112 typically comprises multiple structures each comprising one or more layers of material. For example, a main catheter branch can include a guidewire housing that defines a guidewire lumen, and a main catheter shaft that defines an inflation lumen within which the guidewire housing extends coaxially. In one example, the catheter shaft is a monolayer construction and the guidewire housing is a tri-layer construction that includes material that provides structural integrity to the catheter branch. In other constructions, the structural layer is included in the catheter shaft rather than the guidewire housing.

PEBAX is an example material commonly used to provide such structural integrity to the catheter branch. Typically, the PEBAX layer is the most resistant to bending and torque (i.e., the stiffest material) and has the highest glass transition temperature, requiring the longest amount of time and highest temperature to obtain a heat set. When attempting to heat set the main catheter branch, the PEBAX material (or other material(s) providing the structural integrity) is the target material. In one example, the PEBAX material can be heat set to retain a new shape by exposing the catheter branch to a temperature of about 55° C. for about 12 hours.

Alternatively, heat setting of an arc shape portion in the bifurcation delivery system 110 is done as part of a sterilization process, wherein the curved mandrels are inserted before sterilization. The heat applied during sterilization can be sufficient in some cases to heat set the arc shape of the mandrel in the bifurcation delivery system. The curved mandrels could also be left in the bifurcation delivery system 110 after sterilization as part of the packaging used for the bifurcation delivery system 110. After cooling of the heated bifurcation delivery system and removal of the mandrels 60, 62, the main and side catheter branches 112, 114 retain the curved and linear shapes, respectively, shown in FIG. 6.

The resulting main catheter radius $R_C$ is preferably substantially the same as main mandrel radius $R_{MM}$. In some cases, the radius $R_C$ is greater than the radius $R_{MM}$. In one example, the values of radius $R_C$ and radius $R_{MM}$ are less than about 10 cm. Typically, the values of radius $R_C$ and radius $R_{MM}$ are about 2 to about 5 cm, and more preferably about 3 to about 4.5 cm.

The arrangement of side catheter branch 114 and stent lateral branch opening 52 on the convex side of the arc portion in main catheter branch 112 makes the bifurcation delivery system 110 especially useful for treating vessel bifurcation arrangements such as the arrangement shown in FIG. 2. FIG. 2 illustrates a vessel bifurcation 40 having a branch vessel 44 that branches off from the main vessel 42 along a convex side of the bend in the main vessel 42. The linear shape of side catheter branch 114 in combination with the pre-set curved shape of main catheter branch 112 can provide easier alignment the distal end 120 of the side catheter branch 114 with the branch vessel 44 of FIG. 2.

In another example (not shown), the bifurcation delivery system 110 could be modified for use with a vessel bifurcation having the linear shaped branch vessel extending from a concave side of the main vessel, such as the vessel bifurcation 40 shown in FIG. 4. In a still further embodiment (not shown), the bifurcation delivery system 110 could be modified for use with a vessel bifurcation having the branch vessel extending from the main vessel at a radial location between the inner concave side and the outer convex side of the main vessel. In these alternative embodiments, the side catheter branch 114 and stent lateral branch opening 152 can be arranged at a circumferential position relative to the arc in the main catheter branch to substantially coincide with the orientation of the branch vessel 44 relative to the arc portion in the main vessel 42.

V. The Example Illustrated in FIG. 7-10

Figure 7:
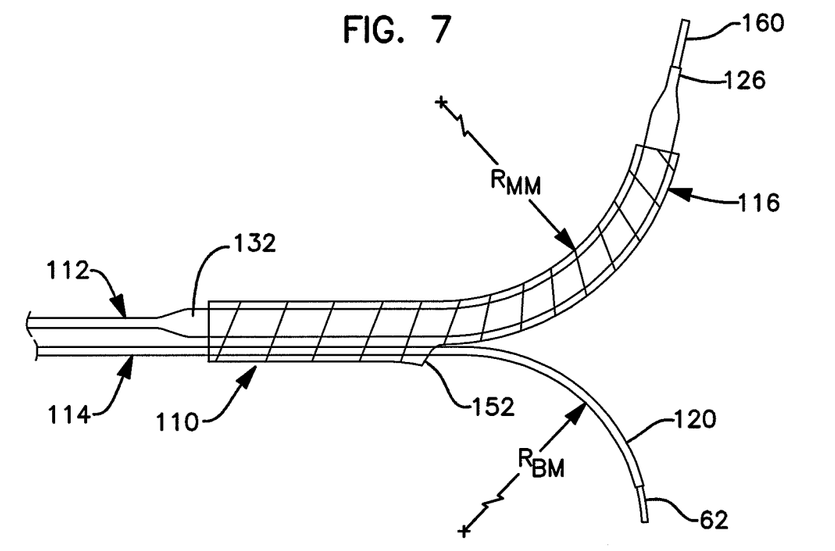
FIG. 7 is a schematic representation of another example bifurcation delivery system having a first portion positioned on a first mandrel having a first arc shape and a second portion positioned on a second mandrel having a second arc shape that is curved in a generally opposite direction from the first arc shape.
Figure 8:
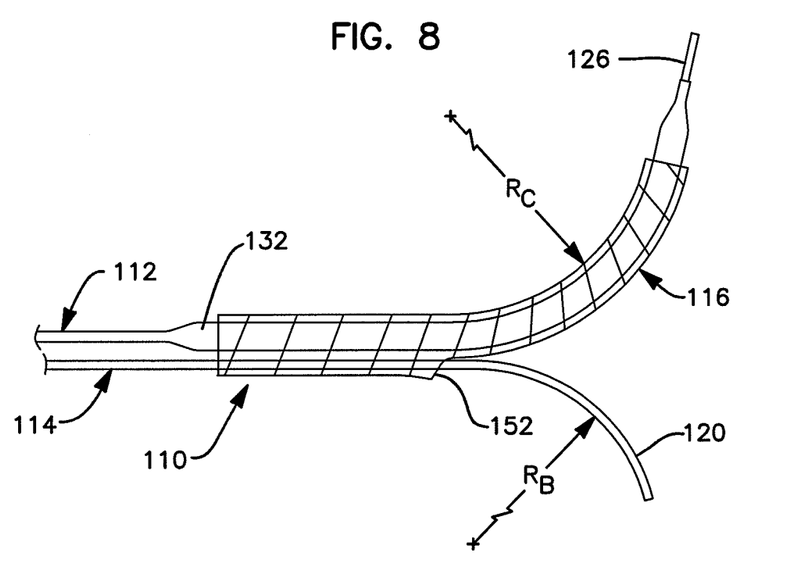
FIG. 8 is a schematic representation of the bifurcation delivery system shown in FIG. 7 with the mandrels removed.

FIGS. 7-8 illustrate aspects of forming arc shape portions in both the main and side catheter branches 112, 114 of bifurcation delivery system 110. Referring to FIG. 7, a main mandrel 160 having a radius of curvature $R_{MM}$ is inserted in the main catheter branch. A branch mandrel 162 having a radius of curvature $R_{BM}$ is inserted into the side catheter branch 114. The mandrels 160, 162 are arranged with their curvature facing in opposite directions while residing within the same plane of the arc shape of main catheter branch 112. The bifurcation delivery system 110 with the mandrels 160, 162 inserted is then heated for a predetermined time and cooled to set the mandrel shapes in the catheter branches 112, 114. The heating and cooling process can follow the conditions described above related to FIGS. 5-6.

The catheter branches 112, 114 are cooled after the heating period to complete heat setting of the arc shape. After cooling of the heated bifurcation delivery system and removal of the mandrels 160, 162, the main and side catheter branches 112, 114 retain the curved shapes shown in FIG. 8. The side catheter branch 114 is arranged along the convex side of the arc portion of main catheter branch 112 and curves in a direction opposite the direction of curvature of the main catheter branch 112.

The resulting main catheter radius $R_C$ is preferably substantially the same as main mandrel radius $R_{MM}$. The resulting branch catheter radius $R_B$ is preferably substantially the same as branch mandrel radius $R_{BM}$. In some cases, the radius' $R_C$ and $R_B$ are greater than the radius' $R_{MM}$ and $R_{BM}$, respectively. Typically, the values of radius' $R_C$ and $R_B$ and radius' $R_{MM}$ and $R_{BM}$ are less than about 15 cm. The values of radius $R_C$ and radius $R_{MM}$ are usually in the range of about 2 to about 10 cm, and more typically in the range of about 3 to about 4.5 cm.

The arrangement of side catheter branch 114 and stent opening 52 on the convex side of the arc in main catheter branch 112 makes the bifurcation delivery system 110 shown in FIG. 8 especially useful for treating vessel bifurcation arrangements such as the arrangement shown in FIG. 2. FIG. 2 illustrates a vessel bifurcation 40 having a branch vessel 44 that branches off from the main vessel 42 along a convex side of the bend in the main vessel 42. The direction of curvature of the arc portion of the side catheter branch 114 can help locate a distal end of the side catheter branch 114 into the branch vessel 44 shown in FIG. 2.

Figure 9:
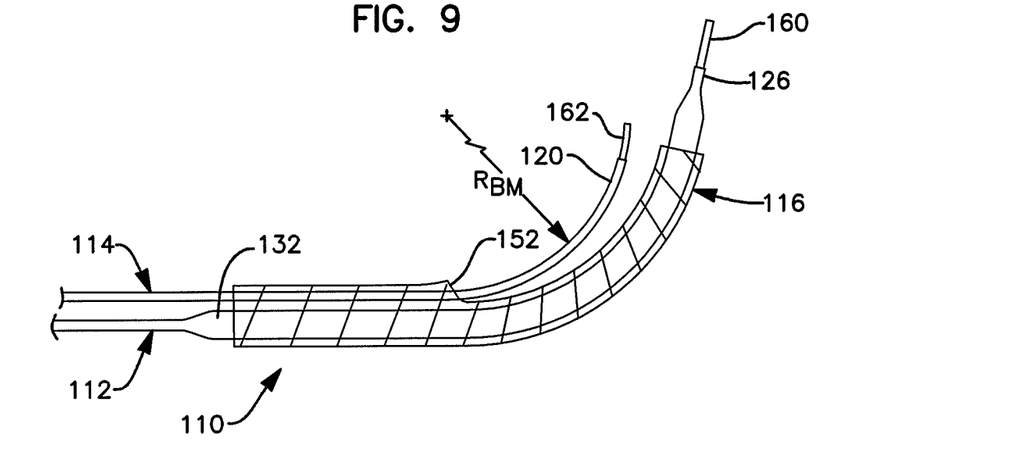
FIG. 9 is a schematic representation of another example bifurcation delivery system having a first portion positioned on a first mandrel having a first arc shape and a second portion positioned on a second mandrel having a second arc shape that is curved in the same general direction as the first arc shape.
Figure 10:
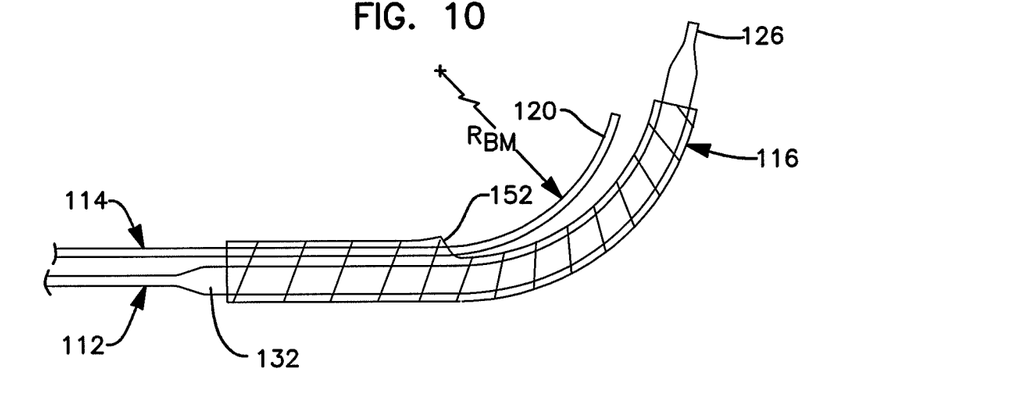
FIG. 10 is a schematic representation of the bifurcation delivery system shown in FIG. 7 with the mandrels removed.

FIGS. 9-10 illustrate aspects of forming arc shape portions in both the main and side catheter branches 112, 114, wherein the curvature of the arc shape portions face in the same direction. Referring to FIG. 9, a main mandrel 160 having a radius of curvature $R_{MM}$ is inserted in the main catheter branch. A branch mandrel 162 having a radius of curvature $R_{BM}$ is inserted into the side catheter branch 114. The mandrels 160, 162 are arranged with their curvature facing in the same direction within the arc portions residing in the same plane. The bifurcation delivery system 110 of FIG. 9 with the mandrels 160, 162 inserted is then heated at a temperature and for a duration (e.g., at those example temperatures and durations described above with reference to FIGS. 5 and 6), and cooled to set the arc shape of the mandrels into the catheter branches 112, 114. The radius' $R_{MM}$ and $R_{BM}$, and the resulting heat set radius' $R_C$ and $R_B$ can be within the range of, for example, those radius values described above with reference to FIGS. 7-8. The side catheter branch 114 is arranged along the concave side of the arc shape portion of main catheter branch 112 and curves in the same direction as the curvature of the main catheter branch 112.

The arrangement of side catheter branch 114 and stent lateral branch opening 52 on the concave side of the arc in main catheter branch 112 makes the bifurcation delivery system 110 shown in FIG. 10 especially useful for treating vessel bifurcation arrangements such as the arrangement shown in FIG. 4. FIG. 4 illustrates a vessel bifurcation 40 having a branch vessel 44 that branches off from the main vessel 42 along a concave side of the bend in the main vessel 42. The direction of curvature of the arc portion of the side catheter branch 114 can help locate a distal end of the side catheter branch 114 into the branch vessel 44 shown in FIG. 4.

Heat setting is just one of many ways of providing an arc shape portion in the main and side catheter branches of those examples described with reference to the Figures. Alternatively, the arc shape in the main and side catheter branches can be achieved by molding the main and side catheter branches with the curved shape. An example molding process capable of providing an arc shaped catheter branch is injection molding. In another example method, the catheter branches are extruded with an arc shape portion therein. In a still further example method, the inner side of the curvature in the catheter branch can be tethered with a tether piece. The tether piece tends to create an arc shape portion along the catheter branch. The tether piece can be integrated as a layer of the catheter branch sidewall in one example construction. Another example method includes chemically swelling or constricting one side of the catheter branch. In another example method, the catheter branches are positioned within a tube(s) having an arc portion and then heat set with a curvature resulting from the arc portion of the tube(s).

VI. Summary and Conclusion

One aspect of the present disclosure relates to a catheter assembly that includes a main catheter branch having a proximal end portion and a distal end portion. The distal end portion of the main catheter branch includes an arc portion. The arc portion includes a curved section, a lumen, an inwardly curved exterior surface side portion of the curved section, an outwardly curved exterior surface side portion of the curved section, and at least one rest side portion. The curved section has first and second ends and an exterior surface. The arc portion maintains the curved section when in a rest state. The lumen is defined within the arc portion and extending between the first and second ends along the curved section. The at least one rest side portion is arranged on the exterior surface between the inwardly and outwardly curved exterior surface side portions. The at least one rest side portion is arranged in a plane parallel with a projection plane. The projection plane is oriented parallel to a plane extending from the inwardly curved side portion to the outwardly curved side portion.

Another aspect of the present disclosure relates to a catheter assembly that includes a main catheter branch and a side catheter branch. The main catheter branch has a proximal end portion and a distal end portion. The distal end portion maintains a curved section when in a rest state. The side catheter branch extends along a portion of the curved section of the distal end portion. The main catheter branch can further include an exterior surface, a lumen defined within the curved section, an inwardly curved exterior surface side portion of the curved section, an outwardly curved exterior surface side portion of the curved section, and at least one rest side portion arranged on the exterior surface between the inwardly and outwardly curved exterior surface side portions. The at least one rest side portion is arranged in a plane parallel with a projection plane, wherein the projection plane is oriented parallel to a plane extending from the inwardly curved side portion to the outwardly curved side portion.

A further aspect of the present disclosure relates to a method of aligning a catheter assembly relative to main and branch vessels of a vessel bifurcation. The catheter assembly includes a main catheter branch having a proximal end portion and a distal end portion. The distal end portion maintains an arc portion, wherein the arc portion includes a curved section having first and second ends and an exterior surface. The arc portion maintains the curved section when in a rest state. A lumen is defined within the arc portion and extends between the first and second ends along the curved section. The arc portion of the main catheter branch includes an inwardly curved exterior surface side portion of the curved section, an outwardly curved exterior surface side portion of the curved section, and at least one rest side portion arranged on the exterior surface between the inwardly and outwardly curved exterior surface side portions. The at least one rest side portion is arranged in a plane parallel with a projection plane, wherein the projection plane is oriented parallel to a plane extending from the inwardly curved side portion to the outwardly curved side portion. The method includes positioning a main guidewire in the main vessel at the vessel bifurcation, the main vessel having an arc portion, and advancing the main catheter branch along the main guidewire to the vessel bifurcation, the main catheter branch rotating relative to the main vessel to self-radial align the arc portion of the main catheter branch with the arc portion of the main vessel.

Another method in accordance with the present disclosure relates to a method of manufacturing a catheter assembly, wherein the catheter assembly includes a main catheter branch. The method includes inserting a first mandrel through the main catheter branch, the first mandrel having an arc portion, heating the main catheter branch while the first mandrel is inserted, cooling the main catheter branch, and removing the first mandrel from the main catheter branch, wherein the main catheter branch retains an arc portion when in a rest state with the first mandrel removed.

It is noted that not all of the features characterized herein need to be incorporated within a given arrangement, for the arrangement to include improvements according to the present disclosure.

We claim:

1. A catheter assembly, comprising:
    a main catheter branch having a proximal end portion and a distal end portion, the distal end portion including a first branch and a second branch, the first branch of the distal end portion including an arc portion, the arc portion comprising:
        a curved section having first and second ends and an exterior surface, the arc portion maintaining the curved section when in a rest state;
        a lumen defined within the arc portion and extending between the first and second ends along the curved section;
        an inwardly curved exterior surface side portion of the curved section;
        an outwardly curved exterior surface side portion of the curved section; and
        at least one rest side portion arranged on the exterior surface between the inwardly and outwardly curved exterior surface side portions, the at least one rest side portion arranged in a plane parallel with a projection plane, the projection plane oriented parallel to a plane extending from the inwardly curved side portion to the outwardly curved side portion;
    a first inflatable balloon positioned on the first branch along the arc portion, wherein the arc portion of the first branch maintains the curved section when the first inflatable balloon is in a deflated state;
    a second inflatable balloon positioned on the second branch, wherein the second inflatable balloon is smaller than the first inflatable balloon; and
    a side catheter branch being generally linear when in a rest state and extending along a portion of the arc portion within a plane that is coplanar with the projection plane extending from the inwardly curved side portion to the outwardly curved side portion.

2. The assembly of claim 1, further comprising a stent having distal and proximal ends and a lateral branch opening positioned at a location between the distal and proximal ends of the stent, the stent positioned along a portion of the arc portion.

3. The assembly of claim 2, wherein the side catheter branch extends-through the lateral branch opening of the stent.

4. The assembly of claim 2, further comprising a sheath surrounding at least a portion of the stent.

5. The assembly of claim 1, wherein the curved section of the arc portion has a radius of between about 1 cm and about 10 cm.

6. The assembly of claim 5, wherein the curved section of the arc portion has a radius of between about 2 cm and about 5 cm.

7. The assembly of claim 1, wherein the side catheter branch extends along at least a portion of the outwardly curved exterior surface side portion of the curved section of the main catheter branch.

8. A catheter assembly, comprising:
    a main catheter branch having a proximal end portion and a distal end portion, the distal end portion including a first branch and a second branch, the first branch of the distal end portion maintaining a curved section when in a rest state;
    a first inflatable member positioned on the first branch along the curved section;
    a second inflatable member positioned on the second branch; and
    a side catheter branch extending along a portion of the curved section of the first branch distal end portion, wherein the side catheter branch maintains a curved section when in a rest state that curves in an opposite direction of the curved portion of the main catheter branch, wherein the first branch and the side catheter branch maintain their curved sections when the first and second inflatable members are in a deflated state, wherein the second branch is positioned radially between the first branch and the side catheter branch.

9. The catheter assembly of claim 8, wherein the main catheter branch further includes:
    an exterior surface;
    a lumen defined within the curved section;
    an inwardly curved exterior surface side portion of the curved section;
    an outwardly curved exterior surface side portion of the curved section; and
    at least one rest side portion arranged on the exterior surface between the inwardly and outwardly curved exterior surface side portions, the at least one rest side portion arranged in a plane parallel with a projection plane, the projection plane oriented parallel to a plane extending from the inwardly curved side portion to the outwardly curved side portion.

10. The catheter assembly of claim 8, wherein the curved section includes an arcuate shape.

11. The catheter assembly of claim 8, further comprising a stent having distal and proximal ends, a sidewall, and a lateral branch opening, the stent positioned along a portion of the curved section and a portion of the side catheter branch, wherein the side catheter branch extends through the lateral branch opening at a location between the proximal and distal ends of the stent.

12. The catheter assembly of claim 8, wherein at least a portion of the first inflatable member extends along at least a portion of the curved section of the distal end portion of the main catheter branch.

13. The catheter assembly of claim 8, wherein the second inflatable member is positioned on the second branch along a portion of the curved section of the distal end portion of the main catheter branch and configured to extend radially outward when inflated relative to a longitudinal axis of the side catheter.

14. A method of aligning a catheter assembly relative to main and branch vessels of a vessel bifurcation, the method comprising:

providing a catheter assembly including a main catheter branch, the main catheter branch having a proximal end portion and a distal end portion, the distal end portion including a first branch and a second branch, the first branch of the distal end portion maintaining an arc portion, the arc portion including a curved section having first and second ends and an exterior surface, the arc portion maintaining the curved section when in a rest state, a lumen defined within the arc portion and extending between the first and second ends along the curved section, an inwardly curved exterior surface side portion of the curved section, an outwardly curved exterior surface side portion of the curved section, and at least one rest side portion arranged on the exterior surface between the inwardly and outwardly curved exterior surface side portions, the at least one rest side portion arranged in a plane parallel with a projection plane, the projection plane oriented parallel to a plane extending from the inwardly curved side portion to the outwardly curved side portion, wherein the catheter assembly further includes a first inflatable balloon positioned on the first branch along the arc portion and a second inflatable balloon positioned on the second branch, wherein the second inflatable balloon is smaller than the first inflatable balloon, wherein the catheter assembly further includes a side catheter branch being generally linear or maintaining a curved section that curves in an opposite direction of the curved portion of the main catheter branch when in a rest state and extending along a portion of the arc portion within the projection plane, wherein the arc portion of the first branch maintains the curved portion when the first inflatable balloon is in a deflated state;

positioning a main guidewire in the main vessel at the vessel bifurcation, the main vessel having an arc portion; and advancing the main catheter branch along the main guidewire to the vessel bifurcation, the main catheter branch rotating relative to the main vessel to self-radial align the arc portion of the main catheter branch with the arc portion of the main vessel.

15. The method of claim 14, wherein radially aligning the arc portion of the main catheter branch with the arc portion of the main vessel radially aligns the side catheter branch with an opening into the branch vessel of the vessel bifurcation.

16. The method of claim 14, further comprising:
positioning a branch guidewire in the branch vessel of the vessel bifurcation; and
advancing the side catheter branch along the branch guidewire to the vessel bifurcation.

17. A catheter assembly, comprising:
a main catheter branch having a proximal end portion and a distal end portion, the distal end portion including a first branch and a second branch, the first branch of the distal end portion maintaining a curved section when in a rest state;
a first inflatable member positioned on the first branch along the curved section, the first inflatable member having a length extending along the first branch;
a second inflatable member positioned on the second branch, the second inflatable member having a length extending along the second branch, wherein in a deflated state, the length of the second inflatable member is less than the length of the first inflatable member; and
a side catheter branch extending along a portion of the curved section of the first branch distal end portion, wherein the side catheter branch is generally linear when in a rest state;
wherein the first branch maintains the curved section when the first inflatable member is in a deflated state.

18. The catheter assembly of claim 17, wherein the main catheter branch further includes:
an exterior surface;
a lumen defined within the curved section;
an inwardly curved exterior surface side portion of the curved section;
an outwardly curved exterior surface side portion of the curved section; and
at least one rest side portion arranged on the exterior surface between the inwardly and outwardly curved exterior surface side portions, the at least one rest side portion arranged in a plane parallel with a projection plane, the projection plane oriented parallel to a plane extending from the inwardly curved side portion to the outwardly curved side portion.

19. The catheter assembly of claim 17, wherein the curved section includes an arcuate shape.

20. The catheter assembly of claim 17, further comprising a stent having distal and proximal ends, a sidewall, and a lateral branch opening, the stent positioned along a portion of the curved section and a portion of the side catheter branch, wherein the side catheter branch extends through the lateral branch opening at a location between the proximal and distal ends of the stent.

21. The catheter assembly of claim 17, wherein at least a portion of the first inflatable member extends along at least a portion of the curved section of the distal end portion of the main catheter branch.

22. The catheter assembly of claim 17, wherein the second inflatable member is positioned on the second branch along a portion of the curved section of the distal end portion of the main catheter branch and configured to extend radially outward when inflated relative to a longitudinal axis of the side catheter.

* * * * *